United States Patent
Lorio

(10) Patent No.: US 9,566,095 B2
(45) Date of Patent: Feb. 14, 2017

(54) SACROILIAC JOINT FASTENER, SYSTEMS, AND METHODS OF USING THE SAME

(71) Applicant: Morgan Packard Lorio, Bristol, TN (US)

(72) Inventor: Morgan Packard Lorio, Bristol, TN (US)

(*) Notice: Subject to any disclaimer, the term of this patent is extended or adjusted under 35 U.S.C. 154(b) by 0 days.

(21) Appl. No.: 14/701,395

(22) Filed: Apr. 30, 2015

(65) Prior Publication Data

US 2015/0313720 A1 Nov. 5, 2015

Related U.S. Application Data

(60) Provisional application No. 61/987,033, filed on May 1, 2014.

(51) Int. Cl.

| A61F 2/44 | (2006.01) |
|---|---|
| A61B 17/70 | (2006.01) |
| A61B 17/84 | (2006.01) |
| A61B 17/86 | (2006.01) |

(52) U.S. Cl.
CPC ......... *A61B 17/7055* (2013.01); *A61B 17/844* (2013.01); *A61B 17/863* (2013.01); *A61B 17/864* (2013.01); *A61F 2/4455* (2013.01); *A61F 2220/0025* (2013.01); *A61F 2250/001* (2013.01)

(58) Field of Classification Search
CPC .. A61F 2002/30995; A61F 2/44; A61F 2/441; A61F 2/442; A61F 2/4425; A61F 2/4405; A61B 17/7064
USPC ........................ 606/105, 313, 247; 623/17.11
See application file for complete search history.

(56) References Cited

U.S. PATENT DOCUMENTS

| 4,874,389 | A  | * | 10/1989 | Downey .................... 623/17.16 |
|---|---|---|---|---|
| 7,611,537 | B2 | * | 11/2009 | Carls et al. ................ 623/17.12 |
| 8,734,462 | B2 | * | 5/2014  | Reiley et al. ................. 606/105 |
| 8,998,923 | B2 | * | 4/2015  | Chirico et al. ............... 606/105 |
| 8,998,925 | B2 | * | 4/2015  | Schwappach ................ 606/105 |
| 9,155,578 | B2 | * | 10/2015 | Chegini et al. |
| 2004/0097927 | A1 | * | 5/2004 | Yeung et al. .................. 606/61 |
| 2005/0065526 | A1 | * | 3/2005 | Drew et al. .................... 606/72 |
| 2005/0085912 | A1 | * | 4/2005 | Arnin et al. ............... 623/17.11 |
| 2005/0113919 | A1 | * | 5/2005 | Cragg .................... A61B 17/70 623/17.11 |
| 2005/0113929 | A1 | * | 5/2005 | Cragg et al. .............. 623/17.16 |
| 2006/0085075 | A1 | * | 4/2006 | McLeer .................... 623/17.12 |

(Continued)

OTHER PUBLICATIONS

International Search Report and Written Opinion in PCT Application No. PCT/US2015/028658 dated Aug. 4, 2015 in 10 pages.

*Primary Examiner* — Eduardo C Robert
*Assistant Examiner* — Michelle C Eckman
(74) *Attorney, Agent, or Firm* — Michael R. Shevlin

(57) ABSTRACT

A sacroiliac ("SI") joint fastener apparatus, systems, and methods of using the device is described. The SI joint fastener apparatus can include a distal segment, a proximal segment, and an expandable portion. The expandable portion can be expanded by reducing the distance between the distal and proximal segments. The SI joint fastener apparatus can be used to fuse two bone portions together. The method can include steps of coupling the fastener apparatus to two bone portions, reducing the distance between the two bone portions to place the portions in compression, and applying an outwardly directed force proximate the location to be fused.

16 Claims, 7 Drawing Sheets

(56) References Cited

U.S. PATENT DOCUMENTS

| | | | |
|---|---|---|---|
| 2006/0155297 A1* | 7/2006 | Ainsworth | A61B 17/025 606/99 |
| 2006/0206209 A1* | 9/2006 | Cragg et al. | 623/17.16 |
| 2006/0276790 A1* | 12/2006 | Dawson | A61F 2/4405 606/86 A |
| 2007/0067034 A1* | 3/2007 | Chirico et al. | 623/17.11 |
| 2007/0198018 A1* | 8/2007 | Biedermann et al. | 606/73 |
| 2008/0140082 A1* | 6/2008 | Erdem et al. | 606/92 |
| 2008/0154305 A1* | 6/2008 | Foley | A61B 17/1604 606/247 |
| 2008/0262502 A1* | 10/2008 | Ainsworth et al. | 606/99 |
| 2009/0099610 A1* | 4/2009 | Johnson et al. | 606/86 R |
| 2009/0125028 A1* | 5/2009 | Teisen et al. | 606/63 |
| 2009/0131992 A1* | 5/2009 | Greenhalgh et al. | 606/313 |
| 2009/0204216 A1* | 8/2009 | Biedermann et al. | 623/17.12 |
| 2009/0259261 A1* | 10/2009 | Reiley | 606/329 |
| 2010/0016905 A1* | 1/2010 | Greenhalgh et al. | 606/313 |
| 2010/0069912 A1* | 3/2010 | McCormack et al. | 606/90 |
| 2010/0070043 A1* | 3/2010 | Kitchen | 623/18.11 |
| 2010/0217325 A1* | 8/2010 | Hochschuler et al. | 606/264 |
| 2010/0228301 A1* | 9/2010 | Greenhalgh et al. | 606/313 |
| 2010/0305703 A1* | 12/2010 | Lin | 623/17.12 |
| 2010/0324607 A1* | 12/2010 | Davis | A61B 17/8685 606/313 |
| 2011/0029019 A1* | 2/2011 | Ainsworth et al. | 606/246 |
| 2011/0257749 A1* | 10/2011 | Fleischmann | 623/17.16 |
| 2012/0101530 A1* | 4/2012 | Robling et al. | 606/279 |
| 2012/0109222 A1* | 5/2012 | Goel et al. | 606/310 |
| 2012/0184993 A1* | 7/2012 | Arambula et al. | 606/246 |
| 2012/0265258 A1* | 10/2012 | Garvey | 606/315 |
| 2012/0265304 A1* | 10/2012 | Mayer | 623/17.12 |
| 2013/0096682 A1* | 4/2013 | Zehavi et al. | 623/17.11 |
| 2013/0310883 A1* | 11/2013 | Levy et al. | 606/313 |
| 2013/0310936 A1* | 11/2013 | Mayer | 623/17.15 |
| 2013/0317617 A1* | 11/2013 | Mayer | 623/17.16 |
| 2014/0012336 A1* | 1/2014 | Biedermann et al. | 606/313 |
| 2014/0350608 A1* | 11/2014 | Goel et al. | 606/279 |
| 2015/0190149 A1* | 7/2015 | Assell et al. | A61B 17/1671 |

\* cited by examiner

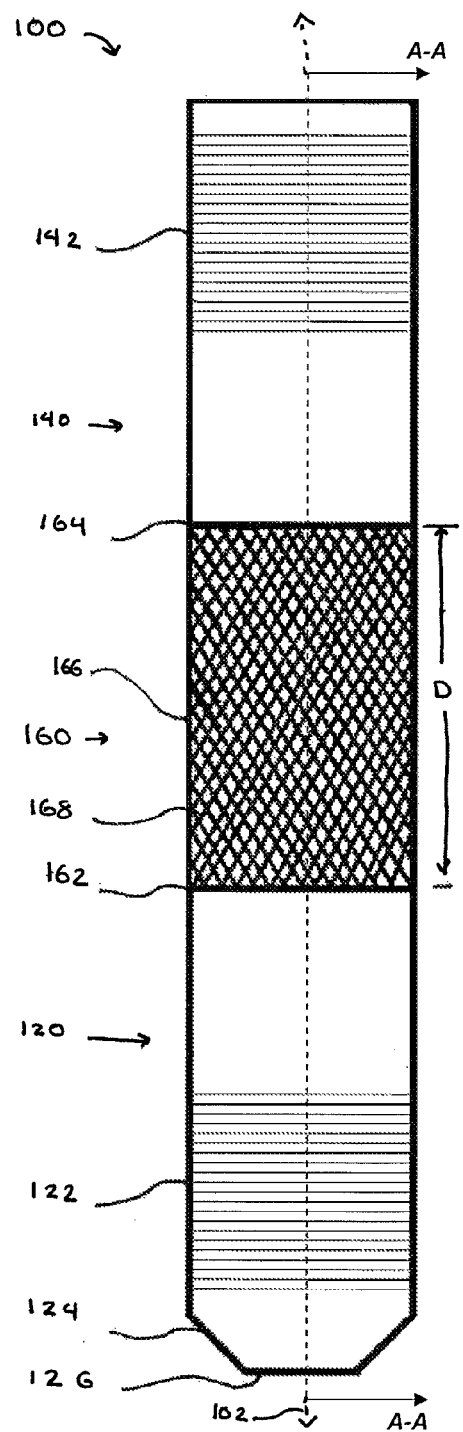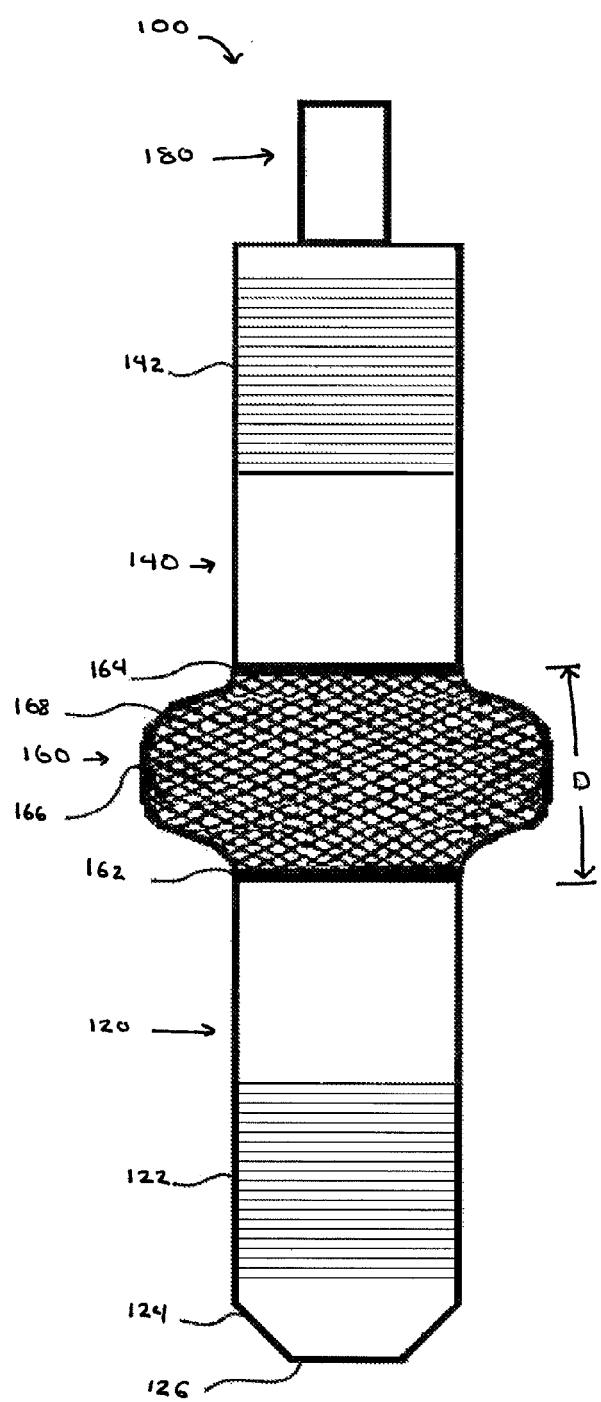
FIGURE 1                    FIGURE 2

SACROILIAC JOINT FASTENER, SYSTEMS, AND METHODS OF USING THE SAME

CROSS REFERENCE TO RELATED APPLICATIONS

The present application claims priority to U.S. Provisional Application No. 61/987,033 filed May 1, 2014, entitled SACROILIAC JOINT FASTENER, SYSTEMS, AND METHODS OF USING THE SAME, the entire contents of both of which are hereby expressly incorporated by reference.

FIELD

The present disclosure relates to bone fasteners, systems and methods, and more specifically, to sacroiliac joint fasteners, systems and methods.

BACKGROUND

The sacroiliac ("SI") joint is a joint located in the pelvis formed by the juncture between the sacrum and the ilium. The SI joint can be a significant contributing factor in many patients having lower back pain. In some studies, dysfunctions of the SI joint, such as degenerative sacroiliitis and sacroiliac disruption, was believed to account for as many as 15% to 22% of patients having chronic lower back pain. In order to relieve pain caused by SI joint dysfunctions, there is a need to develop devices, systems and methods of stabilizing and fusing the SI joint.

SUMMARY

In accordance with the current need to develop devices, systems and methods of stabilizing and fusing the SI joint, as well as generally fusing any two bone portions about a surface, embodiments of fastener apparatuses and methods of using said apparatuses are disclosed herein.

In some embodiments, a fastener apparatus for fusing a joint between a first bone portion and a second bone portion, for example between the ilium and the sacrum, can be used to address this need. The fastener apparatus can include a distal segment, the distal segment having external threading configured to engage osseous tissue of the first bone portion. The fastener apparatus can include a proximal segment designed to engage osseous tissue of the second bone portion. The fastener apparatus can include an intermediate segment having an expandable member between the distal and proximal segments, the expandable member designed to be positioned in the joint between the first bone portion and the second bone portion, wherein the expandable member is designed to expand by movement of the proximal segment and the distal segment relatively toward each other. In some embodiments, movement of the proximal segment relatively toward the distal segment is designed to apply a compressive force to the first and second bone portions.

In some embodiments, the proximal segment can include external threading designed to engage osseous tissue of the second bone portion. The proximal segment can include a flange or washer portion designed to engage an outer surface of the second bone portion. In some embodiments, the expandable member can include a plurality of struts. In some embodiments, the intermediate segment can have no external threading. The intermediate segment can be made from a material different from that of the distal and/or proximal segments. In some embodiments, the proximal segment, the distal segment and the intermediate segment can form an integral unit. In some embodiments, the proximal segment, the distal segment and the intermediate segment each can include a bore which together form a lumen of the fastener apparatus. In some embodiments, the fastener apparatus can include an actuation component extending through the lumen and coupled to the distal segment and/or the proximal segment, the actuation component designed to change a distance between the proximal segment and the distal segment. The actuation component can include a shaft, the distal end of the shaft being coupled to the distal segment. The actuation component can be coupled to the proximal segment. The actuation component can include an internal lumen and openings in fluid communication with the lumen. In some embodiments, the diameter of the distal segment can be greater than the diameter of the proximal segment.

In some embodiments, the fastener apparatus can include a base member including the distal segment comprising external threading configured to engage osseous tissue of the first bone portion. In some embodiments, the fastener apparatus can include a retention member being slideable over the base member and including the proximal segment configured to engage osseous tissue of the second bone portion. In some embodiments, the expandable member can be positionable over the base member between the distal segment and retention member, wherein movement of the retention member toward the distal segment is designed to apply a compressive force to expand the expandable member.

In some embodiments, the base member can include external threading configured to engage internal threading on the retention member. In some embodiments, the intermediate segment can have a diameter which is less than a diameter of a distal portion of the base member. In some embodiments, the retention member can include a flange portion designed to engage an outer surface of the second bone portion.

In some embodiments, a method of fusing a joint between a first bone portion and a second bone portion can be used to address this need. The method can include a step of creating a cavity or bore at the joint. The method can include the step of positioning a fastener apparatus within the bore or cavity, wherein a distal segment of the fastener apparatus engages the first bone portion and a proximal segment of the fastener apparatus engages the second bone portion. The method can include the step of moving the first and second bone portions towards each other by moving the proximal segment relatively toward the distal segment. The method can include the step of applying an outwardly directed force from the fastener apparatus to the first bone portion and the second bone portion.

In some embodiments, the step of positioning the fastener apparatus within the bore or cavity can include engaging threading of the distal segment with the first bone portion and engaging threading of the proximal segment with the second bone portion. In some embodiments, the step of moving the first and second bone portions towards each other can include applying a compressive force to an outer surface of the second bone portion with the distal segment engaging the first bone portion. In some embodiments, the fastener apparatus can include an expandable portion and the step of applying an outwardly directed force can include expanding the expandable portion. In some embodiments, the method can include the step of reaming an at least partially spherical cavity at the joint. In some embodiments, the method can include the step of creating a bore through the first bone portion and the second portion. In some embodiments, the method can include the step of introducing graft material into contact with osseous tissue through the fastener apparatus. In some embodiments, the first bone portion is the sacrum and the second bone portion is the ilium.

In some embodiments, the fastener apparatus can include a base member having a distal segment, a proximal segment and an intermediate segment. The fastener apparatus can include an expandable member sized and shaped to be placed over the base member, the expandable member having an expandable structure with a distal end and a proximal end. The fastener apparatus can include a retention member removably coupled to the proximal segment of the base member. The retention member can be configured to transition the fastener apparatus from a first configuration to a second configuration. In some embodiments, in the first configuration, the distal segment of the base member and the retention member are at a first distance. The expandable member can have a generally cylindrical shape in the first configuration. In some embodiments, in the second configuration, the distal segment of the base member and the retention member are at a second distance. The expandable member can be in a radially expanded position in the second configuration.

In some embodiments, the base member can include a shaft. In some embodiments, the distal segment can have external threading. In some embodiments, the proximal segment can include external threading. In some embodiments, the intermediate segment does not include external threading. In some embodiments, the intermediate segment can have a diameter which is less than a diameter of the distal segment of the base member. In some embodiments, the base member can include a lumen and openings in fluid communication with the lumen, the opening designed to allow fluid to pass to the exterior of the base member. In some embodiments, the expandable structure can include a plurality of struts arranged to expand radially outwardly from a longitudinal axis. In some embodiments, the expandable structure can be manufactured from a material different from that of the base member and/or retention member. In some embodiments, the retention member can include a washer. In some embodiments, the retention member can include a shaft.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

FIG. 1 is a front, schematic view of an embodiment of a fastener apparatus in a first configuration.

FIG. 2 is a front view of the fastener apparatus of FIG. 1 in a second configuration.

DETAILED DESCRIPTION

Figure 3:
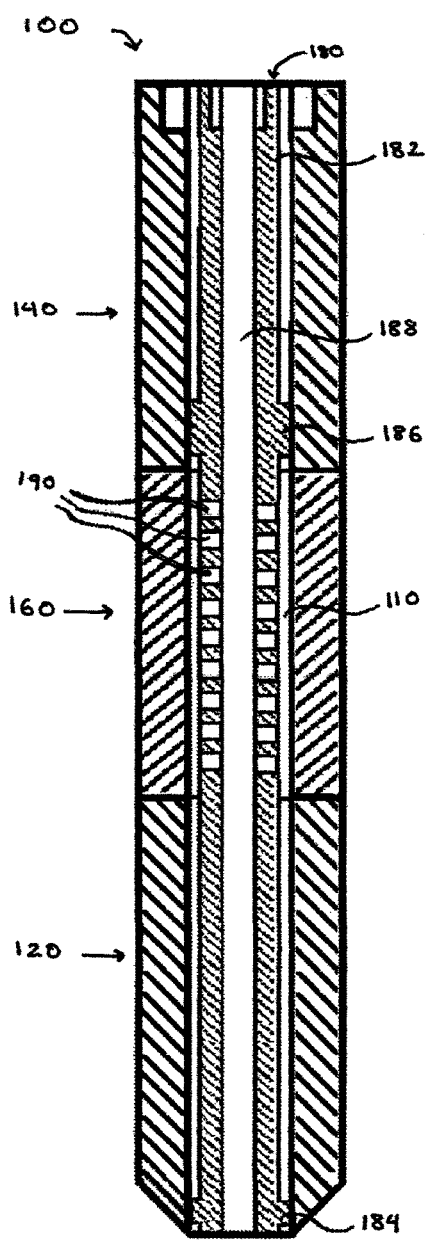
FIG. 3 is a cross-sectional view of the fastener apparatus along line A-A of FIG. 1.

Embodiments of SI joint fasteners, systems and methods of using the devices and systems will now be described with reference to the accompanying figures, wherein like numerals refer to like or similar elements throughout. Although several embodiments, examples and illustrations are disclosed below, it will be understood by those of ordinary skill in the art that the devices, systems and methods described herein extends beyond the specifically disclosed embodiments, examples and illustrations, and can include other uses of the devices, systems and methods and obvious modifications and equivalents thereof. The terminology used in the description presented herein is not intended to be interpreted in any limited or restrictive manner simply because it is being used in conjunction with a detailed description of certain specific embodiments of the devices, systems and methods. In addition, embodiments of the devices, systems and methods can comprise several novel features and no single feature is solely responsible for its desirable attributes or is essential for the devices, systems and methods herein described.

Certain terminology may be used in the following description for the purpose of reference only, and thus are not intended to be limiting. For example, terms such as "above" and "below" refer to directions in the drawings to which reference is made. Terms such as "proximal," "distal," "front," "back," "rear," and "side" describe the orientation and/or location of portions of the components or elements within a consistent but arbitrary frame of reference which is made clear by reference to the text and the associated drawings describing the components or elements under discussion. Such terminology may include the words specifically mentioned above, derivatives thereof, and words of similar import.

In some embodiments, the term "proximal" may refer to the parts of the device and system which are located closer to the operator of the device and system (e.g., the clinician implanting the fastener). The term "distal" may refer to the parts of the device and system which are located further from the operator of the device and system (e.g., the clinician implanting the fastener).

The term "approximately" as used herein represent an amount close to the stated amount that still performs a desired function or achieves a desired result. For example, the term "approximately" may refer to an amount that is within less than 10% of, within less than 5% of, within less than 1% of, within less than 0.1% of, and within less than 0.01% of the stated amount As will be described, the present application relates to bone fasteners, systems and methods of use. More specifically, the present application is directed to SI joint fasteners, systems and methods of implanting and using the fasteners and systems in a patient. The present devices, systems and methods can be used, for example, to fuse the sacrum and ilium together to further aid in stabilizing the joint and providing therapeutic benefit to the patient. Moreover, the devices, systems and methods can advantageously be used as part of a minimally invasive procedure to reduce the risk of complications during and after the procedure has been performed. However, it should be appreciated that while the figures and description herein refer to SI joint fasteners, systems, and methods for using such fasteners and systems, in modified embodiments, the devices, systems and methods can be applied to fuse, or at least stabilize, any other bones about a joint or portions of bone to each other (e.g., around a fracture).

Embodiment of Fastener Apparatus

With reference to FIGS. 1-4, an embodiment of a fastener apparatus 100 is illustrated which can be used, for example, to fuse two bone portions together. The fastener apparatus 100 can be in the form of a screw, bolt, or other type of fastener. With reference first to FIGS. 1 and 2, as shown in the illustrated embodiment, the fastener apparatus 100 can include a distal segment 120 and a proximal segment 140. The fastener apparatus 100 can also include an intermediate, deformable or expandable segment 160 positioned between the distal segment 120 and the proximal segment 140. The distal segment 120 and the proximal segment 140 can be movable relative to each other such that the distance D between the two segments 120, 140 can be altered during operation. For example, the fastener apparatus 100 can have a first configuration, as illustrated in FIG. 1, in which the distal segment 120 and the proximal segment 140 are at a first distance and a second configuration, as illustrated in FIG. 2, in which the distal segment 120 and the proximal segment 140 are at a second distance which is less than the first distance. Conversion of the fastener apparatus 100 from the first configuration to the second configuration can be accomplished using an actuation component 180 coupled to the distal segment 120 and/or the proximal segment 140.

In response to alterations of the distance D between the proximal segment 120 and the distal segment 140, the intermediate segment 160 can deform. For example, as shown in the illustrated embodiment, the intermediate segment 160 can radially expand about the longitudinal axis 102 of the fastener apparatus 100 in response to reduction in distance D between the distal segment 120 and the proximal segment 140. As will be described in further detail below, this can advantageously provide an increase in compression of osseous tissue about the expanded intermediate segment 160 to facilitate fusion about the segment 160.

In alternative embodiments, the intermediate segment 160 may radially expand without the distal segment 120 and proximal segment 140 moving relative to each other. For example, the intermediate segment 160 may be self-expanding from a radially collapsed configuration to a radially expanded configuration, wherein the intermediate segment 160 is held in its radially collapsed configuration using a restraint that may be provided on an interior or an exterior of the intermediate segment 160. As a further example, the intermediate segment 160 may be expandable by applying an outward force from inside of the intermediate segment 160, such as with a balloon or other member that applies a mechanical force to the intermediate segment 160.

With continued reference to FIGS. 1 and 2, the distal segment 120 can include a threaded region 122 along an exterior surface of the segment 120. The threaded region 122 can extend across a part of the exterior surface of the distal segment 120 as shown in the illustrated embodiment or can extend across the entirety of the exterior surface. The external threads of the threaded region 122 can be used to anchor the distal segment 120 to osseous tissue. Accordingly, it should be understood that the external threads of the threaded region 122 are preferably designed to cut into osseous tissue and expedite osseointegration of osseous tissue about the external threads.

The distal segment 120 can include a taper 124 at a distal or leading end of the distal segment 120 to facilitate insertion of the fastener apparatus 100 into osseous tissue. The angle of the taper 124 can vary depending on the specific procedure. For example, in procedures in which the fastener apparatus 100 is inserted into a pre-drilled bore through osseous tissue, the taper 124 can be such that the diameter at the distal or leading end is equal to, or slightly smaller than, the diameter of the pre-drilled bore. The smaller the diameter of the distal or leading end is relative to the diameter of a pre-drilled bore, the easier it can be for the clinician to properly position the fastener apparatus 100 into the bore. In procedures in which the fastener apparatus 100 is used to create such a bore through osseous tissue, the taper 124 can form a pointed edge such that the fastener apparatus 100 can be self-tapping. As shown in the illustrated embodiment, the tapered end 124 can have a frustoconical shape and thus form a flattened surface 126 at a distal-most end. As a result of this flattened surface 126, there is a reduced potential for trauma to other tissue while the fastener apparatus 100 is guided by the clinician towards the target osseous tissue. Of course, the tapered end 124 can take on any other shape including, but not limited to, a rounded shape (e.g., a hemisphere).

Figure 5:
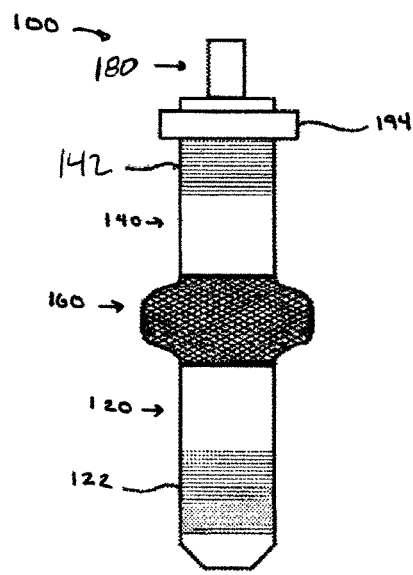
FIG. 5 is a front, schematic view of the fastener apparatus of FIG. 1 having a removable washer.

Similar to the distal segment 120, the proximal segment 140 can include a threaded region 142 across an exterior surface of the segment 140. Threaded region 142 can extend across a part of the exterior surface of the proximal segment 142 as shown in the illustrated embodiment or can extend across the entirety of the exterior surface. External threads of the threaded region 142 can be used to anchor the proximal segment 140 to osseous tissue. Accordingly, similar to external threads of threaded region 122, it should be understood that the external threads of the threaded region 142 are preferably designed to cut into osseous tissue and expedite osseointegration of osseous tissue about the external threads. In some embodiments, the distal segment 120 can be anchored to a first bone, such as the sacrum, and the proximal segment 140 can be anchored to a second bone, such as the ilium. In other embodiments, the proximal segment 120 and the distal segment 140 can be attached to the same bone. Accordingly, upon alteration of the distance D between the distal segment 120 and proximal segment 140, a clinician can advantageously compress or decompress osseous tissue between the two segments 120, 140. Such compression can beneficially enhance fusion of osseous tissue between the proximal segment 120 and distal segment 140. In some embodiments, the proximal segment 140 can include a flange or washer at or near the proximal end of the proximal segment 140. This flange or washer can advantageously contact an outer surface of the osseous tissue to more securable couple the fastener apparatus 100 to osseous tissue and apply compression. In some embodiments, such as that shown in FIG. 5, the flange or washer 194 can be a separate component which can be coupled to the proximal segment 140 and/or the actuation component 180.

As illustrated in FIGS. 1 and 2, the intermediate segment 160 can deform in response to a reduction in distance D between the distal segment 120 and proximal segment 140. Preferably, the intermediate segment 160 can have a first shape which allows the fastener apparatus 100 to be inserted into bone tissue and a second shape which causes additional compression to osseous tissue surrounding the intermediate segment 160. Accordingly, in some embodiments, the intermediate segment 160 can have a first shape or configuration, as illustrated in FIG. 1, in which the intermediate segment 160 is generally cylindrical with a diameter approximately equal to the diameter of the distal segment 120 and/or the proximal segment 140. As should be understood, in some embodiments, the diameter of the intermediate segment 160 can be any value as desired.

The intermediate segment 160 can have a second shape or configuration, as illustrated in FIG. 2, in which the average diameter, maximum diameter or both of the intermediate segment 160 is greater than the diameter of the intermediate segment 160 in the first shape or configuration. For purposes of this discussion, average diameter is the sum of the diameter at the distal end 162, the proximal end 164, and the diameter at the midpoint 166 divided by 3. Accordingly, as shown in the illustrated embodiment, the intermediate segment 160 can expand radially outward from a longitudinal axis 102 of the fastener apparatus 100 as the distance D between the distal segment 120 and the proximal segment 140 is reduced. In order to facilitate conversion of the intermediate segment 160 from the first shape or configuration to the second shape of configuration, the intermediate segment 160, in the first shape or configuration, can be slightly bowed radially outwardly. That is, the diameter of the intermediate segment 160 between the distal end 162 and proximal end 164 can be greater than the diameter of the intermediate segment 160 at the distal end 162, the proximal end 164, or both.

In some embodiments, such as that illustrated in FIGS. 1 and 2, the intermediate segment 160 can have a structure composed of a plurality of struts 168 forming a mesh, wireframe or cage structure attached along a distal end 162 and proximal end 164 of the intermediate segment 160. In response to a compressive force between the distal end 164 and the proximal end 166, or alternatively as a result of an outward force from within the intermediate segment 160 or due to self-expansion, the plurality of struts 168 can deform, preferably radially outwardly, as discussed herein. As should be understood, the intermediate segment 160 can be any other structure, including longitudinally oriented struts or struts oriented in a single direction, which radially outwardly expands relative to a longitudinal axis, for example when the structure is subject to a compressive force generally along, or parallel to, that longitudinal axis. Preferably, in embodiments where the distal segment 120, the proximal segment 140 and the intermediate segment 160 form a monolithic or integral unit, the structure is chosen such that the intermediate segment 160 is generally rigid when subject to forces, such as shear forces, caused by rotation about the longitudinal axis 102. Accordingly, when the fastener apparatus 100 is being screwed into osseous tissue, the intermediate segment 160 can adequately transfer rotational forces from the proximal segment 140 to the distal segment 120 without significant deformation. In some embodiments, the intermediate segment 160 can include threading along a surface, such as an external surface. As shown in the illustrated embodiment, the intermediate segment 160 can have no such threading.

With reference now to FIG. 3, the internal structure of the fastener apparatus 100 is illustrated in more detail. As shown in the illustrated embodiment, the distal segment 120, the proximal segment 140 and/or the intermediate segment 160 can each include a bore which together form a lumen 110 of the fastener apparatus 100. This lumen 110 can be centered along the longitudinal axis 102 of the fastener apparatus 100. It is contemplated that in some embodiments, the lumen 110 can be offset from the longitudinal axis 102 or that more than one lumen can be used. The actuation component 180, such as shaft 182, can be inserted into the lumen 110. The shaft 182 can be coupled to the distal segment 120 via a coupling mechanism 184 positioned along a distal end of the shaft 182. The shaft 182 can also be coupled to the proximal segment 140 via a coupling mechanism 186 positioned along a proximal end of the shaft 182. Other types of actuation components 180 are contemplated. For example, in some embodiments, the actuation component can be a wire or rod (not shown) which can be pulled proximally to transition the fastener apparatus 100 from a first configuration to a second configuration. Moreover, the actuation component 180 can be designed such that the actuation component 180 does not extend beyond the proximal segment 140 while the fastener apparatus is in the second configuration.

In some embodiments, the coupling mechanism 184 can allow rotation between the shaft 182 and distal segment 120 while inhibiting relative translation between the shaft 182 and the distal segment 120. For example, the coupling mechanism 184 can be an annular slot positioned on the distal segment 120 and an annular protrusion positioned on the shaft 182. Accordingly, the shaft 182 can be freely rotated without affecting the distal segment 120 while translation of the shaft 182 can result in translation of the distal segment 120 in the same direction. As shown in the illustrated embodiment, a proximal portion of the shaft 182 can protrude from a proximal end of the proximal segment 140 when the fastener apparatus 100 is placed in the second configuration. Of course, it should also be understood that in some embodiments, the shaft 182 can be sized such that the shaft does not protrude from the proximal end of the proximal segment 140. It is also contemplated that in some embodiments, a proximal portion of the shaft 182 can be removably coupled to the remainder of the shaft 182. Accordingly, in embodiments where the proximal portion of the shaft 182 extends beyond the proximal end of the proximal segment 140, a clinician can advantageously reduce the length of the shaft that protrudes outside the fastener apparatus 100. In some embodiments, the shaft 182 can be rigidly coupled to the distal segment 120.

In some embodiments, the shaft 182 can be removably coupled to the distal segment such that the shaft 182 can be fully removed from the fastener apparatus 100. For example, the coupling mechanism 184 can be converted from an engagement position to a disengagement position. Convertible coupling mechanisms 184 can include fingers or prongs which project radially outward of the shaft 182 in the engaged position and can be pulled radially inward of the shaft 182 when in the disengaged position. Such fingers or prongs can be actuated using a driving apparatus used to deploy the fastener apparatus 100. In some embodiments, locking mechanisms, either internal or external of the fastener apparatus 100 can be used to retain the fastener apparatus 100 in position. Such locking mechanism can include multiple locking positions such that the fastener apparatus 100 can be locked in various positions. For example, the locking mechanism can be a ratchet mechanism, a clip mechanism, or any other locking mechanism as desired.

The coupling mechanism 186 can be threading, a cammed surface, or other structure. For example, the shaft 182 can include exterior threading in an area proximate the proximal segment 140 and the proximal segment 140 can include corresponding interior threading along the lumen 110. Accordingly, rotation of the shaft 182 relative to the proximal segment 140 can result in corresponding translation of the shaft 182 relative to the proximal segment 140. In some embodiments, the coupling mechanism 186 can be used to also "lock" the shaft 182 in position relative to the proximal segment 140 preferably when the fastener apparatus 100 is in the second configuration. For example, in embodiments where the coupling mechanism 186 is threading, the friction between the threads can be sufficient to maintain the shaft 182 in position relative to the proximal segment 140. In some embodiments, a separate locking mechanism, such as a nut, can be attached to the proximal end of the shaft 182 to maintain the shaft 182 in position relative to the proximal segment 140.

The shaft 182 can be cannulated such that it includes an interior lumen 188. The shaft 182 can include one or more openings 190 in fluid communication with the interior lumen 188. The openings 190 can be positioned at any location along the shaft 182. Preferably, at least some openings 190 are placed proximate the intermediate segment 160. Accordingly, when introducing fluid into the lumen 188, such as bone graft material, at least some of the fluid can pass into lumen 110. In embodiments where the intermediate segment 160 comprises an open structure, such as a mesh, wireframe or cage, the fluid can pass out of the intermediate segment 160 and into contact with osseous tissue. It should be understood that the distal segment 120 and the proximal segment 140 can also include openings in fluid communication with lumen 110 for allowing such fluid to pass therethrough and into contact with bone. Accordingly, when bone graft material is used, fusion of the osseous tissue surrounding the fastener apparatus 100 can be facilitated.

Figure 4:
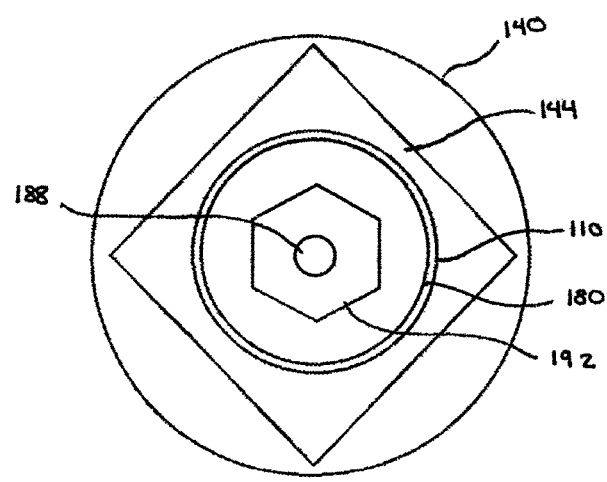
FIG. 4 is a top, schematic view of the fastener apparatus of FIG. 1.

With reference now to FIG. 4, the driving mechanisms of the fastener apparatus 100 are illustrated in more detail. To drive the fastener apparatus 100 into the osseous tissue, the proximal segment 140 can include an internal recess 144 having a cross-sectional shape keyed to a portion of a driving apparatus for the fastener apparatus 100. As shown in the illustrated embodiment, the internal recess 144 has a square cross-sectional shape. However, it should be understood that any cross-sectional shape can be used as desired including star-shaped recesses such as a six-sided star, a double-square, a triple-square, other polygons such as hexagons and octagons, lobular shapes such as trilobular and hexalobular shapes, and any other shape as desired. Moreover, the proximal segment 140 can include an external protrusion (not shown), alone or in combination with the internal recess 144, which can also have a cross-sectional shape keyed to a portion of a driving apparatus. To actuate the actuation component 180 and thus transition the fastener apparatus 100 from the first configuration to the second configuration, or vice-versa, the actuation component 180 can include an internal recess 192 keyed to a portion of a driving apparatus for the fastener apparatus 100. As shown in the illustrated embodiment, the internal recess 192 has a hexagon cross-sectional shape. As with the internal recess 144, internal recess 192 can have any cross-sectional shape as desired including star-shaped recesses such as a six-sided star, a double-square, a triple-square, other polygons such as squares and octagons, lobular shapes such as trilobular and hexalobular shapes, and any other shape as desired. Moreover, the actuation component 180 can include an external protrusion (not shown), alone or in combination with the internal recess 192, which can also have a cross-sectional shape keyed to a portion of a driving apparatus.

The distal segment 120, the proximal segment 140, the intermediate segment 160, and actuation component 180 can be of any desired length, diameter or material. In some embodiments, such as that illustrated in FIGS. 1-4, the distal segment 120, the proximal segment 140 and the intermediate segment 160 can have approximately equal diameters when the fastener apparatus 100 is in the first configuration. It is also contemplated that the proximal segment 140 can have a greater diameter than the distal segment 120 or vice versa. The threading on the distal segment 120 and the proximal segment 140 can have similar pitch or different pitches, diameters, angles, and/or tooth shape. The threading on the distal segment 120 and/or proximal segment 140 can also vary along the length of the threading. For example, a variable pitch can be used. The actuation component 180, such as shaft 182, can have a diameter which is less than the diameter of the lumen 110 in which it is placed. Moreover, as shown in the illustrated embodiment, the length of the distal segment 120 and the proximal segment 140 can be greater than the length of the intermediate segment 160. Generally, the combined lengths of the multiple segments 120, 140, 160 can be chosen such that the distal segment 120 and the proximal segment 140 can span between the two portions of osseous tissue to be coupled and compressed. Moreover, the lengths of the multiple segments 120, 140, 160 can be chosen such that, upon being placed in osseous tissue, the intermediate segment 160 is positioned at a location where additional compression is desired. For example, when used between two bones about a joint, the intermediate segment 160 can be positioned at a joint such as the SI joint and when used between two portions of the same bone, the intermediate segment 160 can be positioned at a location, such as a fracture, of the bone.

In some embodiments, the proximal segment can have a length between approximately 1 millimeter to approximately 30 millimeters, between approximately 2 millimeters to approximately 20 millimeters, between approximately 3 millimeters to approximately 10 millimeters, any length or sub-ranges of lengths within these ranges, or any other length as desired. In some embodiments, the distal segment can have a length between approximately 1 millimeter to approximately 30 millimeters, between approximately 2 millimeters to approximately 20 millimeters, between approximately 3 millimeters to approximately 10 millimeters, any length or sub-ranges of lengths within these ranges, or any other length as desired. In some embodiments, the intermediate segment can have a length, in the first and/or second configurations, between approximately 1 millimeter to approximately 30 millimeters, between approximately 2 millimeters to approximately 20 millimeters, between approximately 3 millimeters to approximately 10 millimeters, any length or sub-ranges of lengths within these ranges, or any other length as desired.

In some embodiments, the intermediate segment, in the first and/or second configuration, can have a diameter between approximately 1 millimeter to approximately 20 millimeters, between approximately 2 millimeters to approximately 15 millimeters, between approximately 3 millimeters to approximately 10 millimeters, any diameter or sub-ranges of diameters within these ranges, or any other diameter as desired. In some embodiments, the intermediate segment can have a maximum diameter in the second configuration which is between approximately 5% to approximately 150%, between approximately 10% to approximately 100%, between approximately 15% to 50%, any percentage or sub-ranges of percentages within these ranges, or any other percentage greater than the maximum diameter in the first configuration.

In any of the embodiments described herein, any of the components such as the distal segment 120, the proximal segment 140 and the intermediate segment 160 can be formed from any type of material. In preferred embodiments, the components, particularly those which remain in the body upon implantation, can be formed from a biocompatible material. Examples of such materials can include metals such as titanium, stainless steel, nitinol and other nickel-titanium alloys, other metal alloys, other shape memory metals, plastics and polymers such as polyetheretherketone, other shape memory polymers, natural materials, synthetic materials, and/or any other material, solely or in combination.

Preferably, the distal segment 120 and the proximal segment 140 are formed from a rigid material capable of maintaining its general structure upon anchoring into osseous tissue and compressing the osseous tissue together. In some embodiments, the intermediate segment 160 can be formed from a material capable of greater deformation than the distal segment 120 and/or proximal segment 140. Accordingly, the intermediate segment 160 can be formed from materials having a lower elastic modulus, a lower bulk modulus, a lower yield strength, and/or other material characteristic. In some embodiments, the intermediate segment 160 can be formed of the same material as the distal segment 120 and/or the proximal segment 140. In such an embodiment, the intermediate segment 160 can have a structure which allows it deform upon application of a compressive force. For example, the strut-based structure as described above.

Embodiment of Modular Fusion Fastener Apparatus

Figures 6, 7:
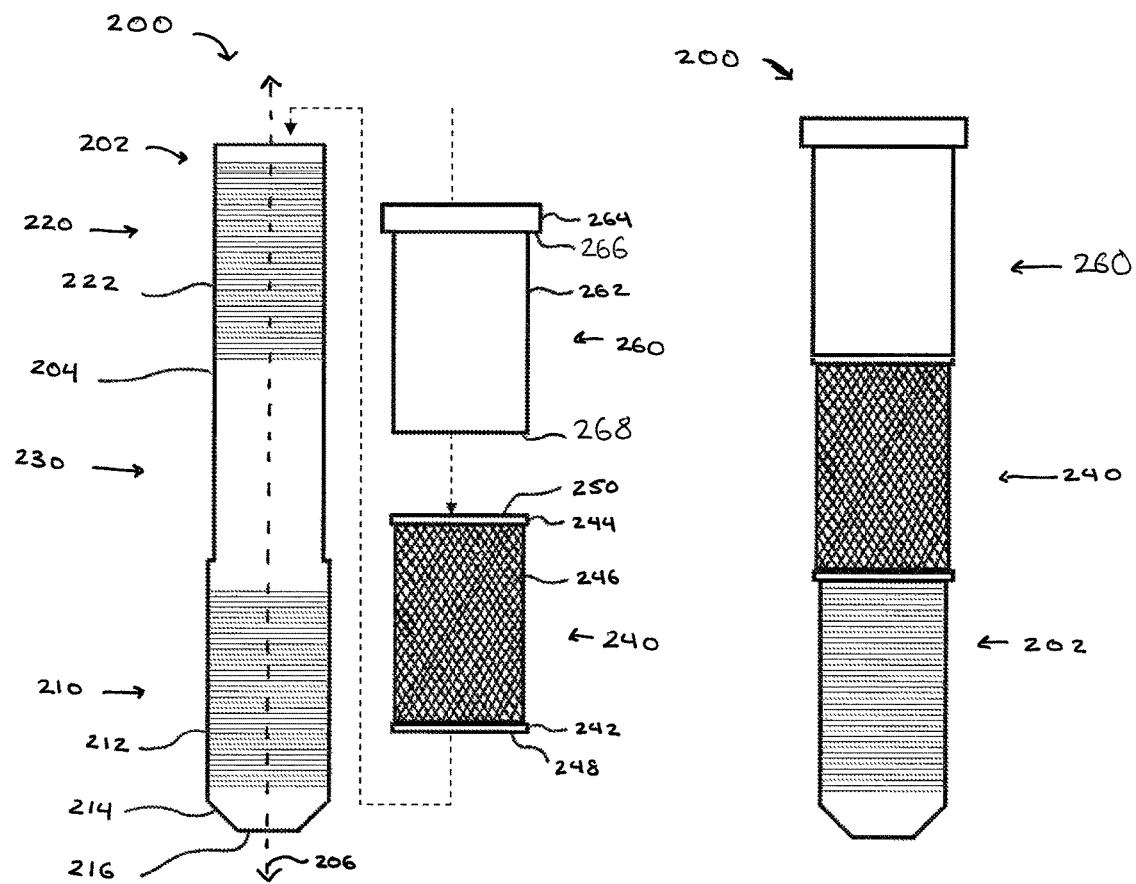
FIG. 6 is a front, schematic view of an embodiment of a fastener apparatus illustrating a base member, an expandable member and a retention member.
FIG. 7 is a front, schematic view of an embodiment of the fastener apparatus of FIG. 6 in an assembled configuration.
Figure 8:
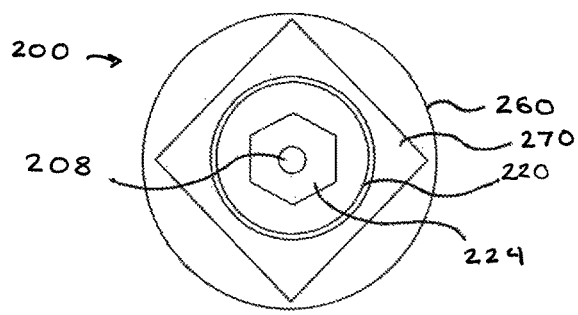
FIG. 8 is a top, schematic view of the fastener apparatus of FIG. 6.
Figure 11:
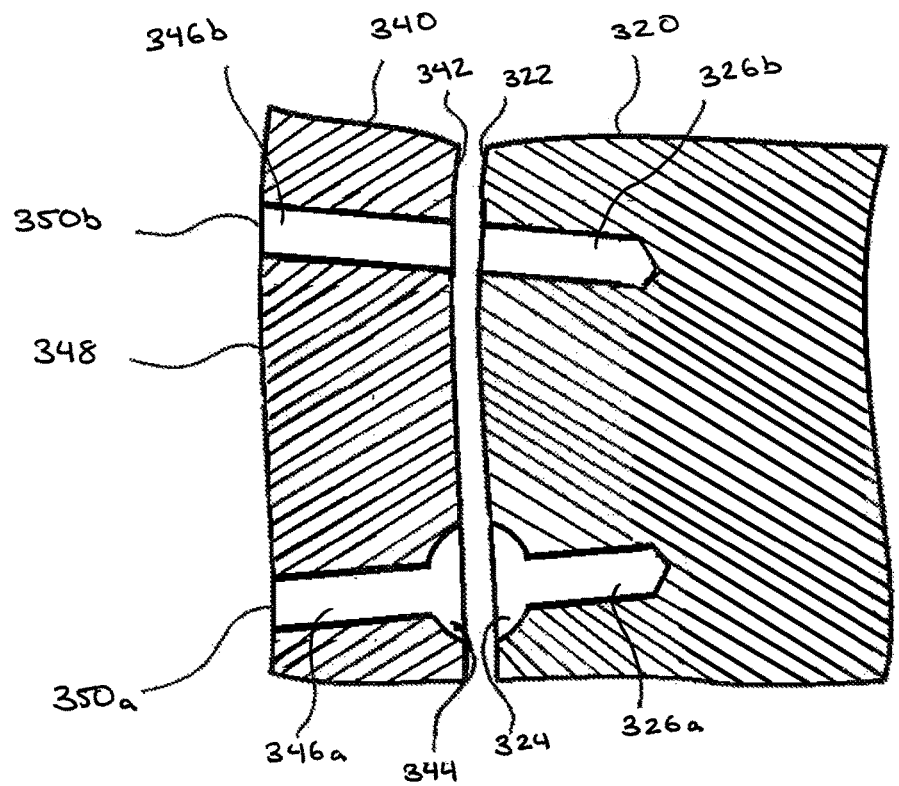
FIG. 11 is a simplified, schematic representation of an SI joint having a cavity and bore.

With reference now to FIG. 6-8, another embodiment of a fastener apparatus 200 is illustrated having modular components. With reference first to FIGS. 6 and 7, as shown in the illustrated embodiment, the fastener apparatus 200 can include a base member 202, an expandable member or sleeve 240 and a retention member 260. The base member 202 can be coupled to osseous tissue and serve as the support structure for the remaining components which may slide over the base member. The expandable member 240 can be placed over the base member 202, either before or after the fastener apparatus 200 is inserted into bone tissue, and deform similar to intermediate segment 160 of fastener apparatus 100. Accordingly, the expandable member 240 can expand or deform when subject to compressive forces, when subject to a radially outward force, or other types of forces as desired. The retention member 260 can be removably coupled to the proximal segment 220 of the base member 202. As shown in the illustrated embodiment, the retention member can be coupled along an exterior surface of the base member 202. In some embodiments, the retention member 260 can be used to apply a compressive force to the expandable member 240. For example, the expandable member 240 can be positioned such that the expandable member 240 contacts osseous tissue (e.g., the surface of bone in which a distal segment 210 is engaged) along a distal end 242 of the expandable member 240 and contacts the retention member 260 along a proximal end 244 of the expandable member 240. Accordingly, when the distance between the osseous tissue and the retention member 260 decreases, the distance between the distal end 242 and proximal end 244 of the expandable member 240 correspondingly decreases. Moreover, the retention member 260 can be used to contact a proximal end surface of osseous tissue such as the dorsum ilii 348 (FIG. 11). For example, the distal face 266 can contact a surface of bone tissue. Accordingly, when the distance between the distal face 266 and the distal segment 210 of the base member 202 is reduced, osseous tissue between the distal segment 210 and the distal face 266 can be placed in compression.

The base member 202 can be a shaft 204 having a distal segment 210, a proximal segment 220 and an intermediate segment 230 positioned between the distal segment 210 and the proximal segment 220. Similar to distal segment 120 of fastener apparatus 100, the distal segment 210 can include a threaded region 212 along an exterior surface of the segment 210. The threaded region 212 can extend across a part of the exterior surface of the distal segment 210 as shown in the illustrated embodiment or can extend across the entirety of the exterior surface. The external threads of the threaded region 212 can be used to anchor the distal segment 210 to osseous tissue. Accordingly, it should be understood that the external threads of the threaded region 212 are preferably designed to cut into osseous tissue and expedite osseointegration of osseous tissue about the external threads.

The distal segment 210 can include a taper 214 at a distal or leading end of the distal segment 210 to facilitate insertion of the fastener apparatus 200 into osseous tissue. The angle of the taper 214 can vary depending on the specific procedure. For example, in procedures in which the fastener apparatus 200 is inserted into a pre-drilled bore through osseous tissue, the taper 214 can be such that the diameter at the distal or leading end is equal to, or slightly smaller than, the diameter of the pre-drilled bore. The smaller the diameter of the distal or leading end is relative to the diameter of a pre-drilled bore, the easier it can be for the clinician to properly position the fastener apparatus 200 into the bore. In procedures in which the fastener apparatus 200 is used to create such a bore through osseous tissue, the taper 214 can form a pointed edge such that the fastener apparatus 200 can be self-tapping. As shown in the illustrated embodiment, the tapered end 214 can have a frustoconical shape and thus form a flattened surface 216 at a distal-most end. As a result of this flattened surface 216, there is a reduced potential for trauma to other tissue while the fastener apparatus 200 is guided by the clinician towards the target osseous tissue. Of course, the tapered end 214 can take on any other shape including, but not limited to, a rounded shape (e.g., a hemisphere).

The proximal segment 220 can include a coupling structure 222 for coupling the proximal segment 220 to the retention member 260. For example, in some embodiments, the coupling structure 222 can be a threaded region across an exterior surface of the segment 220. The threaded region can extend across a part of the exterior surface of the proximal segment 220 as shown in the illustrated embodiment or can extend across the entirety of the exterior surface. External threads of the threaded region can be used to couple the proximal segment 220 to the retention member 260 which can have corresponding threading along an internal surface. In some embodiments, the retention member 260 may not have a corresponding connection structure but can instead be coupled to the coupling structure 222 via a separate fastener, such as a nut with internal threading. For example, the retention member 260 can be slid distally over the proximal segment 220 until a portion of coupling structure 222 is exposed along a proximal end of the retention member 260. The nut can then be coupled to the coupling structure 222 and contact a proximal end of the retention member 260 such that retention member 260 is inhibited from translating proximally over the proximal segment 220. As should be understood, other coupling structures 222 can be used such as bayonet mounts, keyed apertures or any other coupling structure as desired.

The intermediate segment 230 can have a smooth surface to facilitate sliding of the expandable member 240 about the base member 202. In some embodiments, the intermediate segment 230 can include a coupling structure (not shown) such as threading.

Similar to intermediate segment 160 of the fastener apparatus 100, the expandable member 240 can deform in response to compression between the distal end 242 and the proximal end 244. Preferably, the expandable member 240 can have a first shape which facilitates insertion of the expandable member 240 over the base member 202 and a second shape which causes additional compression to osseous tissue surrounding the expandable member 240. Accordingly, in some embodiments, the expandable member 240 can have a first shape or configuration, similar to that of intermediate segment 160 in FIG. 1, in which the expandable member 240 is generally cylindrical with a diameter approximately equal to the diameter of the distal segment 210 and/or the proximal segment 220. As should be understood, in some embodiments, the diameter can be greater than or less than the diameter of the distal segment 210 and/or the proximal segment 220.

The expandable member 240 can have a second shape or configuration, similar to that of intermediate segment 160 in FIG. 2. Accordingly, in the second configuration, the expandable member 240 can expand radially outward from a longitudinal axis 206 of the shaft 204 as the distance between the distal end 242 and the proximal end 244 is reduced. In order to facilitate conversion of the expandable member 240 from the first shape or configuration to the second shape of configuration, the expandable member 240, in the first shape or configuration, can be slightly bowed radially outwardly.

In some embodiments, such as is illustrated in FIGS. 6 and 7, the expandable member 240 can have an expandable structure composed of a plurality of struts 246 forming a mesh, wireframe or cage structure attached along a distal component 248, such as an annular flange or ring, and proximal component 250, such as an annular flange or ring. Such components 248, 250 can facilitate even distribution of compressive forces to the strut 246 structure. In response to a compressive force between the distal component 248 and the proximal component 250, the plurality of struts 246 can deform, preferably radially outwardly, as discussed herein. As should be understood, the expandable member 240 can be any structure that radially outwardly expands relative to a longitudinal axis when the structure is subject to a compressive force generally along, or parallel to, that longitudinal axis.

The retention member 260 can have a shaft portion 262 and a flange or washer portion 264 along the proximal end of the retention member 260. The shaft portion 262 can have a bore or lumen such that the retention member 260 can pass over the proximal segment 220 of the base member 202. In some embodiments, the lumen can include a corresponding connection structure, such as internal threading, to allow the retention member 260 to be coupled to the proximal segment 220 of the base member 202. Accordingly, in such embodiments, rotation of the retention member 260 relative to the base member 202 results in corresponding translation of the retention member 260 relative to the base member 202. In some embodiments, the retention member 260 can be used to contact a proximal end surface of osseous tissue. For example, the distal face 266 of the flange portion 264 can contact a proximal surface of osseous tissue such as the dorsum ilii 348 (FIG. 11). Accordingly, when the distance between the distal face 266 and the distal segment 210 of the base member 202 is reduced, osseous tissue between the distal segment 210 and the distal face 266 can be placed in compression. Accordingly, the fastener apparatus 200 can cause compression of osseous tissue between the distal segment 210 and a distal face 266 of the flange portion 264 of the retention member 260. In some embodiments, the shaft portion 262 can also include external threading (not shown) to engage osseous tissue.

As shown more clearly in FIG. 7, a distal face 268 of the shaft portion 262 can contact the proximal component 250 of the expandable member 240 when the fastener apparatus 200 is assembled. So long as distal component 248 abuts a surface which is fixed relative to base member 202, such as osseous tissue or a face of distal segment 210, as the retention member 260 is moved relative to the base member 202, the expandable member 240 can be compressed thus causing the expandable member 240 to transition from the first configuration to the second configuration.

With reference now to FIG. 8, the driving mechanisms of the fastener apparatus 200 are illustrated in more detail. To drive the base member 202 into the osseous tissue, the proximal segment 220 can include an internal recess 224 having a cross-sectional shape keyed to a portion of a driving apparatus for the fastener apparatus 200. As shown in the illustrated embodiment, the internal recess 224 has a hexagonal cross-sectional shape. However, it should be understood that any cross-sectional shape can be used as desired including star-shaped recesses such as a six-sided star, a double-square, a triple-square, other polygons such as squares and octagons, lobular shapes such as trilobular and hexalobular shapes, and any other shape as desired. Moreover, the proximal segment 220 can be externally keyed, alone or in combination with the internal recess 224, to a portion of a driving apparatus. To drive the retention member 260, the retention member 260 can include an internal recess 270 keyed to a portion of a driving apparatus for the fastener apparatus 200. As shown in the illustrated embodiment, the internal recess 270 has a square cross-sectional shape. As with the internal recess 224, internal recess 270 can have any cross-sectional shape as desired including star-shaped recesses such as a six-sided star, a double-square, a triple-square, other polygons such as hexagons and octagons, lobular shapes such as trilobular and hexalobular shapes, and any other shape as desired. Moreover, the retention member 260 can be externally keyed (not shown) such as along the flange portion 264 to a portion of a driving apparatus. This externally keyed structure can be used alone or in combination with the internal recess 270.

Moreover, as shown in FIG. 8, the shaft 204 can be a cannulated shaft such that it has a lumen 208 into which a fluid can be introduced. This lumen 208 can be in fluid communication with one or more openings (not shown) on the shaft 204. Accordingly, when introducing fluid into the lumen 208, such as bone graft material, at least some of the fluid can pass through the openings and into contact with osseous tissue. Accordingly, when bone graft material is used, fusion of the osseous tissue surrounding the fastener apparatus 200 can be facilitated.

The distal segment 210, proximal segment 220, the intermediate segment 230, the expandable member 240 and the retention member 260 can be of any desired length, diameter or material. In some embodiments, such as that illustrated in FIGS. 6 and 7, the distal segment 210 has a diameter which is greater than the diameter of the proximal segment 220 and the intermediate segment 230. This can facilitate insertion of the expandable member 240 and the retention member 260 over the base member 202. Generally, the combined lengths of the multiple segments 210, 220, 230 can be chosen such that the distal segment 210 and the retention member 260, when attached to the proximal segment 220, can span between the two portions of osseous tissue to be coupled and compressed. Moreover, the lengths of the multiple segments 210, 220, 230 can be chosen such that, upon being placed in osseous tissue, the expandable member 240, when placed over the base member 202, is positioned at a location where additional compression is desired. For example, when used between two bones about a joint, the expandable member 240 can be positioned at a joint such as the SI joint and when used between two portions of the same bone, the expandable member 240 can be positioned at a location, such as a fracture, of the bone.

In any of the embodiments described herein, any of the components such as the distal segment 210, proximal segment 220, the intermediate segment 230, the expandable member 240 and the retention member 260 can be formed from any type of material. In preferred embodiments, the components, particularly those which remain in the body upon implantation, can be formed from a biocompatible material. Examples of such materials can include metals such as titanium, stainless steel, nitinol and other nickel-titanium alloys, other metal alloys, other shape memory metals, plastics and polymers such as polyetheretherketone, other shape memory polymers, natural materials, synthetic materials, and/or any other material, solely or in combination.

Preferably, the base member 202 and the retention member 260 are formed from a rigid material capable of maintaining its general structure upon anchoring into osseous tissue and compressing the osseous tissue together. In some embodiments, the expandable member 240 can be formed from a material capable of greater deformation than the base member 202 and/or retention member 260. Accordingly, the expandable member 240 can be formed from materials having a lower elastic modulus, a lower bulk modulus, a lower yield strength, and/or other material characteristic. In some embodiments, the expandable member 240 can be formed of the same material as the base member 202 and/or retention member 260. In such an embodiment, the expandable member 240 can have a structure which allows it deform upon application of a compressive force. For example, the strut-based structure as described above.

While the fastener apparatuses 100, 200 and associated components are herein described and shown having symmetrical configurations, it should be understood that the fastener apparatuses 100, 200 can have non-symmetrical configurations. In some embodiments, the intermediate segment 160 of fastener apparatus 100 and/or the expandable member 240 of fastener apparatus 200 can, in the second configuration, radially expand in a non-symmetrical manner. For example, along a first plane orthogonal to the longitudinal axis, radial expansion in a first direction may be greater than the radial expansion in a second direction. Moreover, along a second plane orthogonal to the longitudinal axis, radial expansion in the second direction may be greater than the radial expansion in the first direction. As should be apparent, in the second configuration, the intermediate segment 160 and/or the expandable member 240 can take on any shape as desired or required. This can advantageously apply different levels of compression to different portions of osseous tissue.

Embodiment of Method of Fusing Bone Portions

Figure 9A:
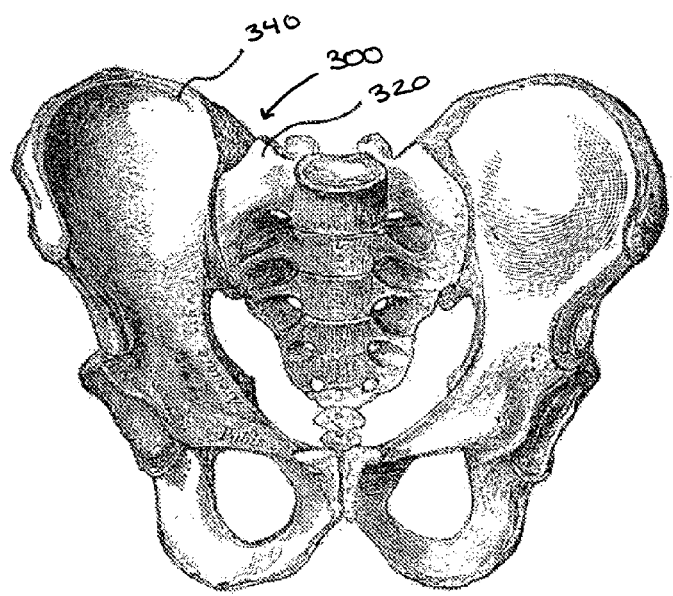
FIG. 9A is a perspective view of an SI joint.
Figure 9B:
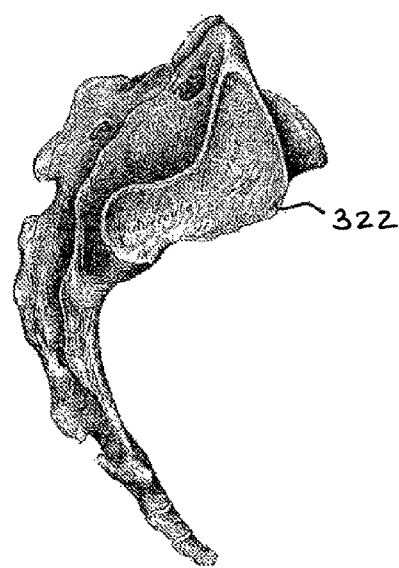
FIG. 9B is a lateral view of a sacrum illustrating an auricular surface.
Figure 9C:
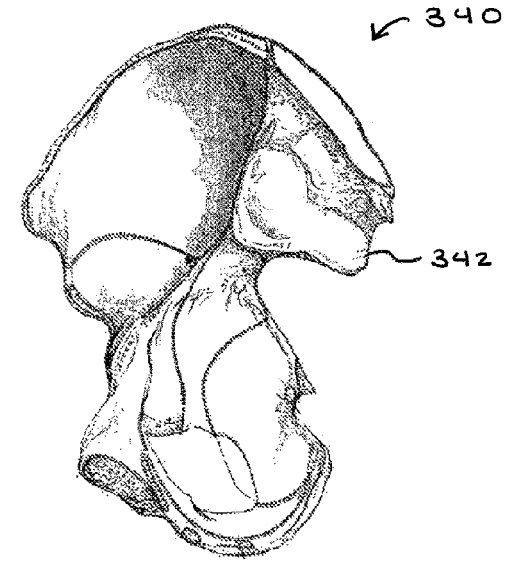
FIG. 9C is a lateral view of an ilium illustrating an auricular surface.
Figure 10:
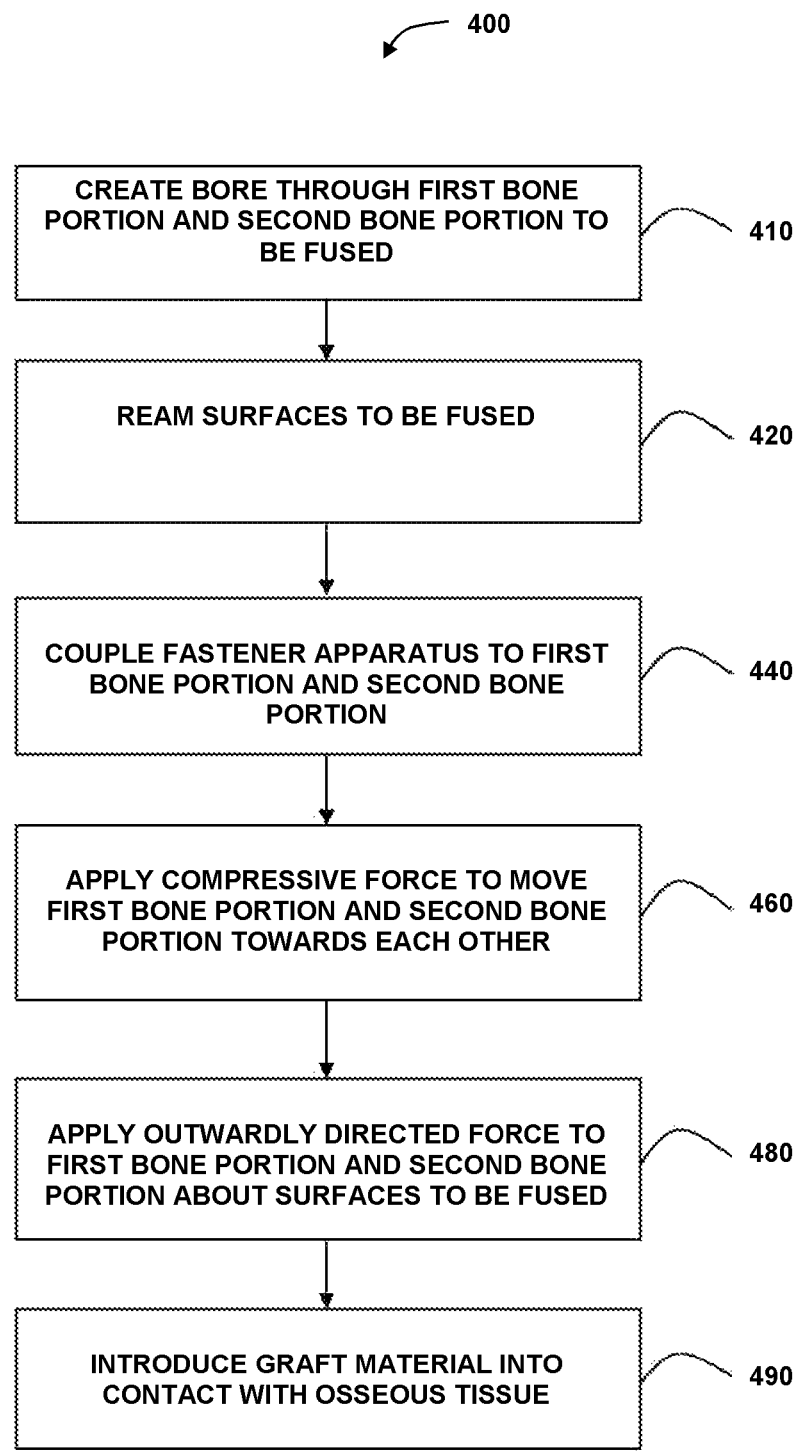
FIG. 10 is a flow diagram of an embodiment of a method for fusing two bone portions about a surface.

FIGS. 9A-9C illustrate the general anatomy about the sacroiliac joint. With reference first to FIG. 9A, the sacroiliac joint 300 is formed by the juncture between the sacrum 320 and the ilium 340 of the pelvis. Generally, the auricular surface 342 of the ilium 340 articulates with a similarly shaped auricular surface 322 of the sacrum 320. The dorsum ilii 348 is the surface opposite the auricular surface 342 on the ala of the ilium, as shown in FIG. 11.

FIGS. 10-14 illustrates steps of a method 400 of fusing two bone portions about a surface using a fastener apparatus such as fastener apparatuses 100, 200. For example, the steps of method 400 can be performed to fuse a joint between a first bone portion and a second bone portion. During step 410, a clinician can create a bore through a first bone portion and a second bone portion to be fused. As illustrated in FIG. 11, this bore can be created across a joint or the surfaces to be fused. In some embodiments, one or more bores 326a, 326b can be formed partially through the sacrum 320 and one or more bores 346a, 346b can be formed through the ilium 340. The one or more bores 346a, 346b through the ilium 340 can be created from the dorsum ilii 348 or other surface opposite the auricular surface 342. Accordingly, one or more entry openings 350a, 350b can be formed on the dorsum ilii 348 through which a fastener apparatus, such as fastener apparatus 100, 200, can be inserted. As shown in the illustrated embodiment, the bores 326a, 326b, 346a, 346b are oriented such that they are generally orthogonal to the surfaces 322, 342 to be fused. This can advantageously more evenly distribute compressive forces along these surfaces 322, 342 and osseous tissue. Moreover, as shown in the illustrated embodiment, the bores 326a, 326b in the sacrum 320 are collinear with corresponding bores 346a, 346b through the ilium 340 to facilitate passage of a fastener apparatus into the sacrum 320 and ilium 340.

In some embodiments, one or more bores can be formed such that they are not generally orthogonal to these surfaces 322, 342 as desired. For example, such bores can be created to apply compressive forces to different portions of the surfaces 322, 342. Such bores can also be created if surgery is facilitated by creation of such bores. In some embodiments, one or more of the bores in the sacrum 320 can be offset with respect to corresponding bores in the ilium 340.

During step 420, a clinician can ream the joint between the two surfaces to be fused together. This step can be performed simultaneously as step 410. As illustrated in FIG. 11, a cavity 324 can be formed in the sacrum 320 along the auricular surface 322. In alternative to or in combination with cavity 324, a cavity 344 can be formed in the ilium 340. As shown in the illustrated embodiment, the two cavities 324, 344 have a partially spherical shape. Of course, the cavities 324, 344 can be of any shape or size as desired. In some embodiments, the cavities can be disc or pancake shaped. The cavities 324, 344 can have a shape which is similar to the shape of the expanding portion of the fastener apparatus, such as intermediate segment 160 and expandable member 260 of fastener apparatuses 100, 200 respectively, to allow the fastener apparatus to expand within the cavities 324, 344. Preferably, the cavities 324, 344 have a size which is approximately equal to the size of the expanding portion of the fastener apparatus such that, when the expanding portion is in an expanded state, the expanding portion contacts and applies a force to interior surfaces of the cavities 324, 344. This can potentially enhance stability of the joint. Of course, the cavities 324, 344 can be of any size. For example, the cavities 324, 344 can be larger or smaller than the expanding portion.

These cavities 324, 344 can be formed with a reaming tool. The reaming tool can have an elongate member sized to fit within the bores 326a, 326b, 346a, 346b. In some embodiments, the elongate member can be a cannula having an internal lumen. The reaming tool can include a cutting member which extends radially outwardly from the longitudinal axis of the elongate member. The cutting member can be designed such that the clinician can control the outward extension. Accordingly, as the elongate member is rotated within the bores 326a, 326b, 346a, 346b, the cutting member can remove osseous tissue. The clinician can then progressively increase the outward extension of the cutting member such that additional osseous tissue is progressively removed as the elongate member is rotated. By changing the outward extension and/or positioning the cutting member along the bores 326a, 326b, 346a, 346b, a clinician can form cavities 324, 344 having different shapes and sizes. Other methods of forming cavities 324, 344 can be used as desired.

Moreover, while FIG. 11 illustrates a bore created across a joint or the surfaces to be fused, it should be understood that, during step 420, the bore can be created between the first bone portion and the second bone portion. For example, with respect to FIG. 11, a bore (not shown) can be formed vertically between the surfaces 322, 342, along the interface or gap between the surfaces 322, 342.

Figure 12:
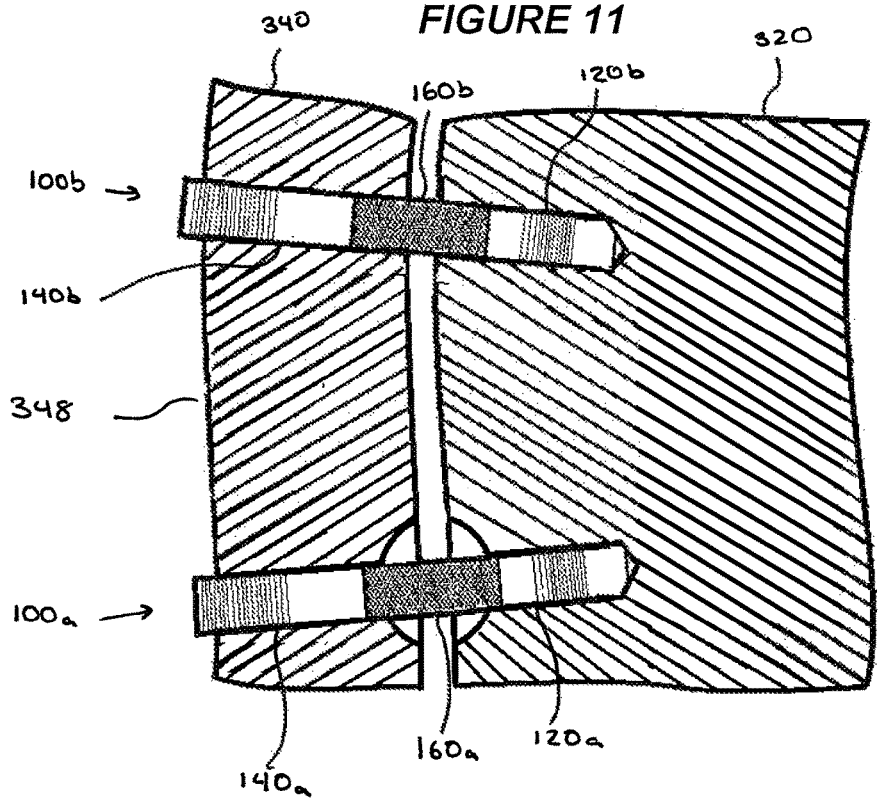
FIG. 12 is a simplified, schematic representation of the SI joint of FIG. 11 having fastener apparatuses, in a first configuration, coupled therein.

During step 440, a clinician can couple one or more fastener apparatuses to the first bone portion and the second bone portion. As illustrated in FIG. 12, one or more fastener apparatuses 100a, 100b can be inserted through openings 350a, 350b and into the bores 326a, 326b, 346a, 346b formed during the second step 420. The fastener apparatuses 100a, 100b can have a similar structure to fastener apparatus 100 described in connection with FIGS. 1-5 above. The fastener apparatuses 100a, 100b can be positioned such that the distal segments 120a, 120b are anchored or coupled to the sacrum 320 and the proximal segments 140a, 140b are anchored or coupled to the ilium 340. Moreover, the intermediate segment 160a, 160b can be positioned proximate the two surfaces 322, 342 to be attached. As shown in the illustrated embodiment, a portion of the proximal segments 140a, 140b can slightly protrude from the dorsum ilii 348. In some embodiments, proximal segments 140a, 140b sit flush with the dorsum ilii 348 or placed further within bores 346a, 346b such that proximal segments 140a, 140b do not protrude from the dorsum ilii 348.

Figure 13:
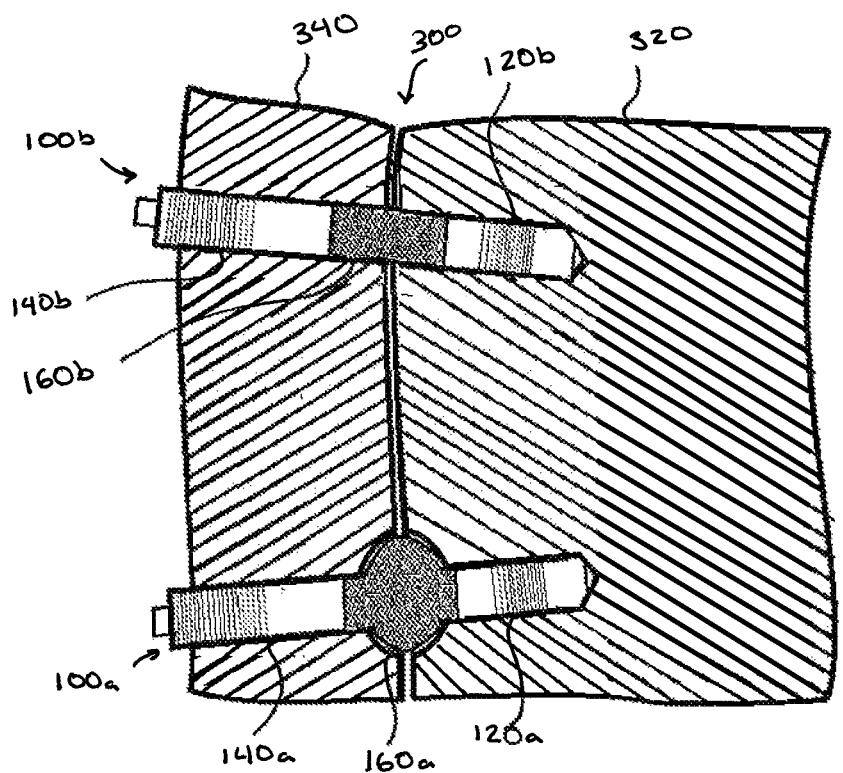
FIG. 13 is a simplified, schematic representation of the SI joint of FIG. 12 where the fastener apparatuses are in a second configuration.

During step 460, a clinician can apply a compressive force to move the first bone portion and the second bone portion closer towards each other along the longitudinal axis of the fastener apparatus. In some embodiments, the first bone portion and the second bone portion can be pulled into contact with each other such that a compressive force is applied to the bone portions. As illustrated in FIG. 13, the one or more fastener apparatuses 100a, 100b can be actuated as described above such that the apparatuses 100a, 100b transition from a first configuration to a second configuration in which the distal segments 120a, 120b and proximal segments 140a, 140b are closer together. Accordingly, as a result in the reduction in distance between the distal segments 120a, 120b and the proximal segments 140a, 140b, and their attachment to the sacrum 320 and the ilium 340 respectively, the distance separating the sacrum 320 and ilium 340 is reduced.

In some embodiments, the distance can be chosen such that at least a portion of surfaces 322, 342 are placed into contact thus causing some compression of the SI joint 300. For example, in some embodiments, the reduction in distance between the distal segments 120a, 120b and the proximal segments 140a, 140b can be between approximately 0.1 mm to approximately 10 mm, between approximately 0.5 mm to approximately 5 mm, between approximately 0.5 mm to approximately 2.5 mm, or any other distance as desired. Moreover, the reduction in distance of any fastener apparatus can be different from the reduction in distance of any other fastener apparatus.

In embodiments where the fastener apparatus used is similar to fastener apparatus 200, rather than reducing the distance between the distal segments 120a, 120b and the proximal segments 140a, 140b, the clinician can instead attach a retention member, similar to retention member 260 to the proximal end of the fastener apparatus. The clinician can then translate the retention member distally along the fastener apparatus such that the retention member contacts the dorsum ilii 348. Since the distal segments of the fastener apparatus are anchored or coupled to the sacrum 320, further distal translation can apply a compressive force to the dorsum ilii 348 such that the distance separating the sacrum 320 and the ilium 340 is reduced.

In the alternative, the fastener apparatus can be chosen such that the distance between the sacrum 320 and the ilium 340 does not change but compression is maintained. For example, the intermediate segments 160a, 160b can be used between the sacrum 320 and the ilium 340 to prevent, or at least decrease, the reduction in distance between the two bones. Accordingly, the bone portions are maintained in compression.

During step 480, a clinician can apply an outwardly directed force, relative to a longitudinal axis of the fastener apparatuses 100a, 100b, to the first bone portion and the second bone portion about surfaces to be fused. Such force can increase the amount of compression of bone tissue. Moreover, such force can provide additional stabilization around the surfaces to be fused. This can be particularly advantageous before the surfaces are fused. As illustrated in FIG. 13, the one or more fastener apparatuses 100a, 100b can be actuated as described above such that the apparatuses 100a, 100b transition from a first configuration to a second configuration in which the intermediate segments 160a, 160b expand outwardly. Accordingly, as a result in the expansion of the intermediate segments 160a, 160b, the intermediate segments 160a, 160b can apply an outwardly directed force on surfaces of the sacrum 320 and the ilium 340. In some embodiments, step 480 can occur simultaneously with step 460.

As shown in the illustrated embodiment, due to the shape of the bore in which it is placed, the intermediate segment 160b of fastener apparatus 100b does not appear to expand; however, it applies an outwardly directed force, primarily parallel to surfaces 322, 342. Additionally, the force can have a greater magnitude than that applied by intermediate segment 160a. Accordingly, it should be understood that the shape of the cavities 324, 344, or the lack thereof, can be advantageously chosen to alter the direction and magnitude of the force applied.

Figure 14:
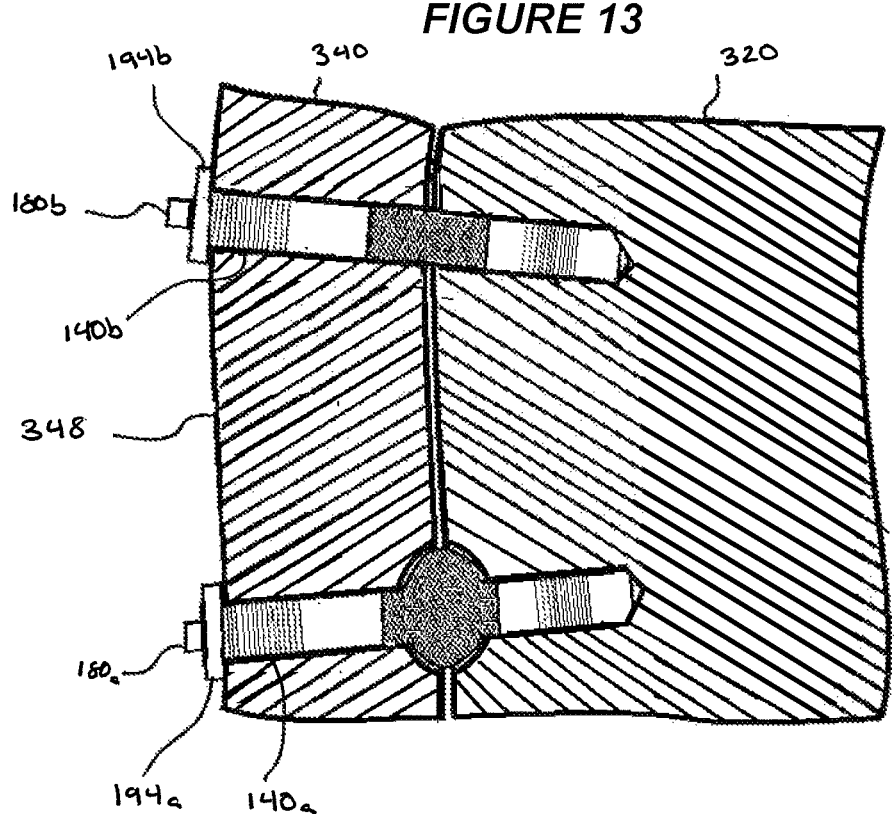
FIG. 14 is a simplified, schematic representation of the SI joint of FIG. 13 having washers coupled to the fastener apparatuses.

With reference to FIG. 14, one or more washers 194a, 194b can be attached to the fastener apparatuses 100a, 100b to more securably couple the fastener apparatuses 100a, 100b to the sacrum 320 and the ilium 340. As shown in the illustrated embodiment, washers 194a, 194b are coupled to the proximal segments 140a, 140b such that a face of the washers contacts the dorsum ilii 348 of the ilium 340. It should be understood that the washers 194, 194b can also attach to the actuation components 180a, 180b of the fastener apparatuses 100a, 100b. Attachment to the actuation components 180a, 180b can reduce the likelihood that the fastener apparatuses 100a, 100b transition towards the first configuration as a result of the forces applied.

During step 490, a clinician can introduce graft material, such as bone graft material, to a target location, such as a specific portion of osseous tissue. Similar to fastener apparatus 100, one or more fastener apparatuses 100a, 100b can include lumens such that fluids can be introduced through the lumens and out of openings such that the introduced fluid contacts osseous tissue. In some embodiments, bone graft material can be introduced to facilitate and/or expedite formation of osseous tissue thus fusing portions of the sacrum 320 and ilium 340 together.

While the method 400 is described in connection with the sacroiliac joint 300 in FIGS. 11-14, it should be understood that this is by way of example only. The method 400 can be applied to fusing of any two or more bones together about two or more joints as well as to fusing two or more bone portions together about a surface, such as a fracture. In addition, in some embodiments, the fastener apparatus can be inserted generally parallel to the surfaces to be fused. For example, the fastener apparatuses can be inserted vertically between the surfaces 322, 342, along the interface or gap between the surfaces 322, 342. Moreover, it should be understood that any of the steps as described herein are optional.

Variations, Modifications, and Combinations

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

What is claimed is:

1. A fastener apparatus for fusing a joint between a first bone portion and a second bone portion, the apparatus comprising:
   a distal segment, the distal segment having external threading configured to engage osseous tissue of the first bone portion;
   a proximal segment, the proximal segment having external threading configured to engage osseous tissue of the second bone portion; and
   an intermediate segment having an expandable member between the distal and proximal segments configured to be positioned in the joint between the first bone portion and the second bone portion,
   wherein the proximal segment, the distal segment and the intermediate segment each include a bore which together form a lumen of the fastener apparatus;
   an actuation component extending through the lumen, the actuation component including:
      a shaft;
      a distal coupling mechanism positioned along a distal end of the shaft coupled to the distal segment, the distal coupling mechanism being configured to allow rotation between the shaft and distal segment while inhibiting relative translation between the shaft and the distal segment; and
      a proximal coupling mechanism positioned along a proximal end of the shaft coupled the proximal segment, the proximal coupling mechanism being configured to allow translation between the shaft and the proximal segment,
      wherein, the actuation component configured to translate the proximal coupling mechanism toward the distal coupling mechanism by rotation of the shaft and change a distance between the proximal segment and the distal segment;
   wherein the expandable member is configured to expand by movement of the proximal segment and the distal segment-relatively toward each other using the actuation component;
   wherein movement of the proximal segment relatively toward the distal segment is configured to apply a compressive force to the first and second bone portions.

2. The fastener apparatus according to claim 1, wherein the proximal segment includes a flange or washer portion configured to engage an outer surface of the second bone portion.

3. The fastener apparatus according to claim 1, wherein the expandable member includes a plurality of struts.

4. The fastener apparatus according to claim 1, wherein the proximal segment, the distal segment and the intermediate segment form an integral unit.

5. The fastener apparatus according to claim 1, wherein the actuation component has an internal lumen and openings in fluid communication with the lumen.

6. The fastener apparatus according to claim 1, wherein the intermediate segment does not comprise external threading.

7. The fastener apparatus according to claim 1, wherein the intermediate segment includes a material different from at least one of the distal and proximal segments.

8. The fastener apparatus according to claim 1, wherein a diameter of the distal segment is greater than a diameter of the proximal segment.

9. A method of fusing a joint between a first bone portion and a second bone portion, the method comprising:
   creating a cavity or bore at the joint;
   positioning a fastener apparatus within the bore or cavity, the fastener apparatus comprising:
      a distal segment, the distal segment having external threading configured to engage the first bone portion;
      a proximal segment, the proximal segment having external threading configured to engage the second bone portion; and an intermediate segment having an expandable member between the distal and proximal segments configured to be positioned in the joint between the first bone portion and the second bone portion, wherein the proximal segment, the distal segment and the intermediate segment each include a bore which together form a lumen of the fastener apparatus;

an actuation component extending through the lumen, the actuation component including:
 a shaft;
 a distal coupling mechanism positioned along a distal end of the shaft coupled to the distal segment, the distal coupling mechanism being configured to allow rotation between the shaft and distal segment while inhibiting relative translation between the shaft and the distal segment; and
 a proximal coupling mechanism positioned along a proximal end of the shaft coupled the proximal segment, the proximal coupling mechanism being configured to allow translation between the shaft and the proximal segment,
 wherein, the actuation component configured to translate the proximal coupling mechanism toward the distal coupling mechanism by rotation of the shaft and change a distance between the proximal segment and the distal segment;

wherein the distal segment of the fastener apparatus engages the first bone portion and the proximal segment of the fastener apparatus engages the second bone portion;

moving the first and second bone portions towards each other by moving the proximal segment relatively toward the distal segment with the actuation component; and applying an outwardly directed force from the fastener apparatus to the first bone portion and the second bone portion.

10. The method according to claim 9, wherein positioning the fastener apparatus within the bore or cavity includes engaging threading of the distal segment with the first bone portion and engaging threading of the proximal segment with the second bone portion.

11. The method according to claim 9, wherein moving the first and second bone portions towards each other includes applying a compressive force to the second bone portion and the first bone portion.

12. The method according to claim 9, wherein applying an outwardly directed force includes expanding the expandable portion.

13. The method according to claim 9, comprising reaming an at least partially spherical cavity at the joint.

14. The method according to claim 9, comprising creating a bore through the first bone portion and the second portion.

15. The method according to claim 9, further comprising introducing graft material into contact with osseous tissue through the fastener apparatus.

16. The method according to claim 9, wherein the first bone portion is the sacrum and the second bone portion is the ilium.

* * * * *